US012758721B2

(12) United States Patent
Trexler et al.

(10) Patent No.: US 12,758,721 B2
(45) Date of Patent: Oct. 13, 2026

(54) THERAPEUTIC POWDER APPLICATOR

(71) Applicant: Davol Inc., Warwick, RI (US)

(72) Inventors: Jonathan Bruce Trexler, Rehoboth, MA (US); Oliver Sowerby, Cambridge (GB); Steve McLellan, Cambridge (GB); Michael Herd, Cambridge (GB); Charles Lowndes, Cambridge (GB); Jon Jamin, Cambridge (GB)

(73) Assignee: Davol Inc., Warwick, RI (US)

( * ) Notice: Subject to any disclaimer, the term of this patent is extended or adjusted under 35 U.S.C. 154(b) by 443 days.

(21) Appl. No.: 17/361,280

(22) Filed: Jun. 28, 2021

(65) Prior Publication Data

US 2021/0402106 A1 Dec. 30, 2021

Related U.S. Application Data

(60) Provisional application No. 63/046,176, filed on Jun. 30, 2020.

(51) Int. Cl.
*A61M 13/00* (2006.01)
*A61B 17/12* (2006.01)

(52) U.S. Cl.
CPC ....... *A61M 13/00* (2013.01); *A61B 17/12181* (2013.01); *A61B 2017/12004* (2013.01)

(58) Field of Classification Search
CPC .. A61M 13/00; A61M 11/001; A61M 11/003; A61M 16/201; A61M 16/208; A61M 2205/075; A61M 2205/3334; A61M 2206/16; A61M 11/02; A61M 2202/064; A61M 2205/3331; A61M 2205/586; A61M 11/00; A61M 11/006–008; A61M 11/06; A61M 11/08; A61B 17/12181; A61B 2017/12004; A61B 2017/00522;
(Continued)

(56) References Cited

U.S. PATENT DOCUMENTS 2,987,221 A * 6/1961 Milton .................. B05B 7/1404 222/1
4,184,258 A 1/1980 Barrington et al.
4,859,121 A 8/1989 Deysson et al.
(Continued)

FOREIGN PATENT DOCUMENTS

JP 2016-538895 A 12/2016
JP 2018-518310 A 7/2018
(Continued)

OTHER PUBLICATIONS

International Search Report and Written Opinion, mailed Dec. 6, 2021 for International Application No. PCT/US2021/039467.
(Continued)

*Primary Examiner* — Kevin C Sirmons
*Assistant Examiner* — Leah J Swanson
(74) *Attorney, Agent, or Firm* — Wolf, Greenfield & Sacks, P.C.

(57) ABSTRACT

Therapeutic powder applicators and their methods of operation are described. In some embodiments, a first flow of gas may flow through a distal porous portion of a chamber containing a therapeutic powder. This gas may fluidize and entrain the therapeutic powder and flow the entrained powder through an outlet that is in fluid communication with the chamber.

51 Claims, 14 Drawing Sheets

(58) Field of Classification Search
CPC ... B05B 7/1413; B05B 7/1463; B05B 11/062; B05B 15/63
See application file for complete search history.

(56) References Cited

U.S. PATENT DOCUMENTS

| | | | | |
|---|---|---|---|---|
| 5,273,531 | A * | 12/1993 | Knopfler | A61M 31/00 604/212 |
| 5,816,509 | A * | 10/1998 | Ahn | B05B 7/1404 241/58 |
| 6,454,141 | B1 | 9/2002 | Breen et al. | |
| 7,455,248 | B2 * | 11/2008 | Kablik | A61L 31/042 239/362 |
| 9,205,207 | B2 | 12/2015 | Ji | |
| 2002/0144680 | A1 * | 10/2002 | Nilsson | A61M 15/005 128/203.15 |
| 2007/0235029 | A1 * | 10/2007 | Zhu | A61M 16/107 128/203.15 |
| 2011/0251580 | A1 | 10/2011 | Greenhalgh et al. | |
| 2013/0218072 | A1 | 8/2013 | Kubo | |
| 2013/0274690 | A1 | 10/2013 | Greenhalgh et al. | |
| 2015/0094649 | A1 * | 4/2015 | Gittard | A61M 13/00 428/402 |
| 2016/0375202 | A1 * | 12/2016 | Goodman | A61L 26/0023 |
| 2018/0193574 | A1 | 7/2018 | Smith et al. | |
| 2018/0339144 | A1 | 11/2018 | Greenhalgh et al. | |
| 2019/0232030 | A1 | 8/2019 | Pic et al. | |
| 2020/0061310 | A1 | 2/2020 | Goodman et al. | |
| 2021/0275157 | A1 * | 9/2021 | Pic | A61B 17/00491 |

FOREIGN PATENT DOCUMENTS

| | | | |
|---|---|---|---|
| JP | 2020-503145 | A | 1/2020 |
| KR | 10-2013716 | B1 | 8/2019 |
| WO | WO-9008723 | A1 * | 8/1990 |
| WO | WO 2019/092689 | A1 | 5/2019 |
| WO | WO 2021/178853 | A1 | 9/2021 |

OTHER PUBLICATIONS

Extended European Search Report dated May 17, 2024 for European Application No. EP 21833460.5.

* cited by examiner

THERAPEUTIC POWDER APPLICATOR

CROSS-REFERENCE TO RELATED APPLICATIONS

This application claims the benefit of priority under 35 U.S.C. § 119(e) of U.S. Provisional Application Ser. No. 63/046,176, filed Jun. 30, 2020, the disclosure of which is incorporated herein by reference in its entirety.

FIELD

Disclosed embodiments are related to therapeutic powder applicators and their related methods of use.

BACKGROUND

Powder applicators are used in many different applications to apply various types of powders to a desired surface including the delivery of therapeutic powders to a desired location of a subject for therapeutic purposes. Powders that are delivered using these applicators tend to be lightweight low density powders with a Hausner ratio between 1.00 and 1.18. Some applicators fluidize a powder by directing a flow a gas either onto a top free surface of the powder with all of the bulk disposed vertically below the applied flow of gas during operation or through an entire bulk of a mass of particles such as from a side opposite an opening in a chamber containing a powder. However, these types of constructions may be unable to adequately fluidize powders which are more difficult to fluidize than those noted above.

SUMMARY

In one embodiment, a therapeutic powder applicator includes: a chamber configured to contain a therapeutic powder, where at least a distal portion of the chamber includes a plurality of pores; a first pressurized gas source in fluid communication with the chamber through the plurality of pores of the distal portion of the chamber; and an outlet in fluid communication with the chamber.

In one embodiment, a therapeutic powder applicator includes: a chamber configured to contain a therapeutic powder, where at least a distal portion of the chamber includes a plurality of pores; and a first gas inlet; an outlet in fluid communication with the chamber, where the first gas inlet is in fluid communication with the outlet through the plurality of pores of the distal portion of the chamber.

In one embodiment, a method of applying a therapeutic powder includes: flowing a first gas flow through a plurality of pores of a distal portion of a chamber containing the therapeutic powder; entraining the therapeutic powder in the first gas flow; and flowing the entrained therapeutic powder through an outlet in fluid communication with the chamber.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
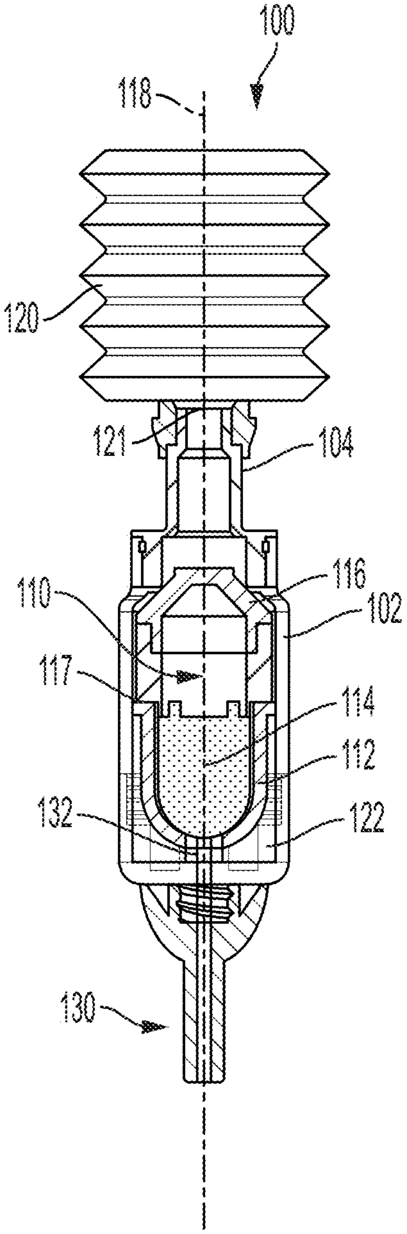
FIG. 1 is a cross sectional view of one embodiment of a powder applicator.

Therapeutic powders used for different applications may vary both in particle size and density. These properties impact the flow character, or flowability, of the powder. The Hausner ratio can be used to assess the flowability of a powder and is calculated by dividing the measured tapped density of a powder by its bulk density. Generally, the lower the Hausner ratio, the better the flowability. For example, powders with a Hausner ratio between 1.00 and 1.18 may be considered to exhibit excellent to good flow characteristics whereas powders with a Hausner ratio above 1.18 exhibit fair to poor flow characteristics. There may also be other powder characteristics such as particle morphology, basic flowability energy BFE (mJ), aerated energy AE (mJ), aeration ratio (AE), wall friction angle (WFA), compression percent, static charge, moisture content, and other appropriate parameters which may result in reduced overall flowability of a powder. Particles with poor flowability are relatively difficult to fluidize, making them ill-suited for certain application methods.

Hemostatic powders are therapeutic powders used to manage or stop bleeding. These powders are commonly applied via applicators, which may use a stream of gas to direct the powder towards and onto a bleed site. Existing applicators use relatively high pressure and/or high velocity gas, and are generally effective at fluidizing and applying hemostatic powders with relatively small particle sizes and/or relatively low densities. Such hemostatic powders may exhibit Hausner ratios between 1.00 and 1.18. However, these small particle size and/or low density hemostatic powders may be ineffective at breaking the surface tension of flowing blood, and therefore may not reach a desired location beneath the flowing blood. Thus, the use of larger and/or more dense powders capable of breaking the surface tension of flowing blood may be advantageous in certain applications. In addition to the particle size, density and Hausner ratio, other particle characteristics, including but not limited to, particle morphology, basic flowability energy BFE (mJ), aerated energy AE (mJ), aeration ratio (AE), wall friction angle (WFA), compression percent, static charge, and moisture content may also improve a hemostatic powders' ability to penetrate blood, while reducing the powders' ability to be effectively fluidized with existing high pressure and/or velocity applicators. However, the inventors have recognized that existing high pressure applicators are generally ineffective at fluidizing and applying powders with one or more of the above noted characteristics which may improve their ability to penetrate blood.

In view of the above, the Inventors have recognized the benefits of an improved therapeutic powder applicator capable of handling a variety of different types of powders. Such an applicator may be configured to effectively fluidize and apply therapeutic powders across a range of pressures and/or velocities, ranging from the relatively high pressures and/or velocities used by existing applicators to relatively low pressures and/or velocities below those of existing applicators. In some embodiments, such an applicator may also enable therapeutic powders to be applied with variable spread, for example enabling targeted applications to both smaller and/or larger areas. Thus, in some embodiments, operation of an applicator may be varied to effectively dispense a hemostatic powder with a desired precision and/or control to a targeted location which may vary in size from broad areas to small areas. In contrast, typical applicators use relatively high pressure and/or high velocity gas which are generally effective at fluidizing and applying hemostatic powders to broad target areas.

In view of the above, the Inventors have recognized the benefits of an improved therapeutic powder applicator capable of delivering a variety of different types of powders in a controllable fashion. In some instances, this may enable delivery to either broad and/or small target areas. In such an embodiment, an applicator may be configured to effectively control the delivery area by controlling a pressure and/or velocity of a gas used to entrain the particles, which in some instances may be relatively low pressures and/or velocities compared to typical applicators.

In certain embodiments, a therapeutic powder applicator includes a chamber configured to contain a powder, such as a therapeutic powder (e.g. a hemostatic powder). A portion of, or the entire, chamber may be made of a porous material. A first pressurized gas source may be in fluid communication with the chamber though the porous material of the chamber. Additionally, an outlet of the chamber may be in fluid communication with an interior volume of the chamber. In such an embodiment, a first flow of gas from the first pressurized gas source may flow into the chamber through the porous material. Once in the chamber, the flow of gas may fluidize and entrain the powder prior to flowing out of the outlet of the chamber to dispense the powder from the applicator. Depending on the particular embodiment, the flow of gas may be delivered to the chamber such that it is flowed into the chamber through the porous material forming a portion of the chamber either in a direction that is angled relative to a direction of flow of gas and entrained particles out of the chamber and/or at a location that is proximate to a stationary distal portion of the chamber disposed between the opening and a proximal end of the chamber located opposite the opening. Additionally, in some embodiments, this distal portion of the chamber may be configured such that when the device is operated, the distal portion of the chamber and the opening may be oriented at least partially vertically downwards relative to a local direction of gravity to maintain powder adjacent to the opening and the porous portion of the chamber through which the gas flows.

In some embodiments it may be desirable to further increase the turbulence of a flow of gas into a chamber and thus a mixing of the gas with particulates within the chamber. In such an embodiment, an applicator may include a vortex chamber disposed adjacent to an opening of the chamber. The vortex chamber may be configured to concentrate the incoming gas flow through the porous material forming a portion of the chamber near the outlet location. Without wishing to be bound by theory, this may improve aeration and fluidation of the powder near the outlet which may increase the amount of material delivered per actuation.

In certain embodiments it may be desirable to entrain a fluidized powder in a separate flow of gas. Such an arrangement may help with dispensing a fluidized powder from an outlet of an applicator in a desired dispersion pattern. In such an embodiment, the applicator may include at least a second flow of gas that is separate from a first flow of gas that passes through a chamber of the applicator to fluidize a powder contained therein as described above. During operation the first flow of gas with the entrained powder may be combined with the second flow of gas at a point downstream from the chamber. Thus, the entrained powder may be dispensed through an outlet of the applicator by the combined flow of the first and second flows of gas. It should be understood that the pressure source for this second flow path may either be the same or different from the pressure source used to fluidize the powder.

During application, it may be desirable to adjust the spread or coverage of a powder applied via an applicator. For example, it may be desirable to go from a smaller spread such that the powder may be dispensed onto a first smaller area and a larger spread where the powder may be dispensed onto a second larger area. Additionally, in some instances it may be desirable to dispense a larger amount of powder, whereas in other instances, it may be desirable to dispense a smaller amount of powder. In some embodiments, the above noted dispensing parameters may be adjusted by adjusting the relative flow rate of gas through the first and second flow paths of an applicator described above. This may be accomplished by changing a relative flow resistance of one or both flow paths (e.g. a variable flow resistance valve), changing a flow rate of a gas from an associated pressure source, and/or any other appropriate method for controlling a relative flow rate of gas between the different flow paths. For instance, in one exemplary embodiment, a variable resistance valve may be fully opened to permit a maximum flow through the second flow path in a first operating mode, partially closed to permit a reduced flow through the second flow path in a second operating mode, and fully closed to prevent the flow of gas through the second flow path in a third operating mode.

As noted above, at least a portion of a chamber may be made from a porous material. In some embodiments, the porous material may be configured such that the porous material is permeable to a gas from a first pressurized gas source and impermeable to a powder with a predetermined range of particle sizes. As such, the porous material may retain the powder within the chamber and prevent the powder from back flowing towards the associated pressurized gas source. The applicator may be configured such that the powder resides in the chamber when the applicator is not in operation (e.g., when the first pressurized gas source is not being operated to deliver a gas to the chamber). The porous material may correspond to any appropriate material and/or construction including a plurality of open pores that extend from one side of the material to another opposing side of the material. In some embodiments the plurality of holes may be formed in the material by drilling, molding, laser ablation, or using any other suitable manufacturing technique. In other embodiments, the porous material may be a porous membrane which may correspond to a woven, non-woven, or other appropriate membrane construction. Additionally, in some instances, the diffusion properties of a porous membrane may be altered by sintering the porous membrane. Thus, in some embodiments, a porous material may include a sintered porous membrane. In view of the above, it should be understood that any appropriate type of porous material with a suitable pore density and pore size may be used with the various embodiments described herein as the disclosure is not limited in this respect.

As described above, either an entire chamber, or only a portion of the chamber may be constructed of a porous material. In embodiments, where only a portion of the chamber is porous, a remainder of the chamber may be constructed of any suitable non-porous material including plastics, glasses, metals, etc. The porous and non-porous portions of the chambers may have interfacing surfaces. In certain embodiments, the porous and non-porous portions of the chamber may be selectively coupleable at the interfacing surfaces. This arrangement may enable the chamber to be selectively opened and closed, enabling therapeutic powder to be added or removed as desired. Such embodiments may be configured for reuse. In other embodiments, the various portions of the chamber may be integrally formed with one another and/or permanently connected. In such embodiments, the chamber may be provided with a specific amount or dosage of a desired therapeutic powder, and once that dosage is exhausted, the chamber may be removed from the applicator, disposed of, and optionally replaced by a new chamber including a new dosage of therapeutic powder. Accordingly, an applicator may be configured with either single use or multiple uses as the disclosure is not limited in this fashion.

The applicators disclosed herein may be used to fluidize and dispense a wide range therapeutic powders, with varied particle sizes and densities. The inventors have shown through testing that the lower pressures and/or velocities provided by certain embodiments described herein may enable the use of relatively larger size and/or higher density powders. For example, the applicator may be configured to fluidize powders having a particles size that is greater than or equal to 100 μm, 200 μm 300 μm and/or any other appropriate size. A powder may also have a particle size that is less than or equal to 700 μm, 600 μm 500 μm and/or any other appropriate size. Combinations of the above noted ranges are contemplated including, for example, a particle size of a powder that is between or equal to 100 μm and 700 μm. In addition to the above, in some embodiments, the applicator disclosed may enable the use of a combination of multiple types of powder particles, each consisting of similar or different particle properties, i.e. size, density, etc. In addition to the above, in some embodiments, the powders may have a Hausner ratio greater than 1.18, although it should be appreciated that the applicator may be configured to fluidize and dispense powders with a Hausner ratio below 1.18 as well. For example, a Hausner ratio of one or more powders contained within an applicator may be greater than or equal to 1.18, 1.2, 1.3, and/or any other appropriate ratio. Correspondingly, the Hausner ratio may be less than or equal to 1.4, 1.3, 1.2, and/or any other appropriate ratio. Combinations of the foregoing are contemplated including, for example, Hausner ratios between or equal to 1.18 and 1.4 though ratios both greater than and less than those noted above are also contemplated. Additionally, while specific particle sizes are given above, particles with sizes both greater than and less than those noted above are also contemplated as the disclosure is not so limited.

As noted above, in some embodiments, an applicator may be configured to utilize a pressure lower than that of standard applicators. Appropriate pressures that may be provided from a pressure source to a chamber and/or other portion of an applicator may be greater than or equal to 2 millibar (mbar), 3 mbar, 5 mbar, 10 mbar, 20 mbar, and/or any other appropriate pressure. The pressure supplied by the pressure source may also be less than or equal to 40 mbar, 30 mbar, 20 mbar, 2 mbar, and/or any other appropriate pressure. Combinations of foregoing are contemplated including, for example, a pressure source that is configured to provide a flow of gas at a pressure between or equal to 2 mbar and 40 mbar. Of course, different combinations of the above ranges as well as ranges of pressures that are both greater than and less than those noted above are also contemplated as the disclosure is not so limited.

The pressure sources described herein may correspond to any appropriate type of pressure source capable of providing a flow of pressurized gas to one or more portions of a powder applicator. Appropriate pressure sources may include, but are not limited to, compressible bellows, a gas canister, a centralized pressure source such as a pressurized gas port, a pump, and/or any other appropriate pressure source capable of providing a pressurized gas to an applicator. The pressure source may provide a flow of atmospheric air, $CO_2$, hydrofluoroalkane, and/or any other appropriate gas. Depending on the particular embodiment, the pressure source may be directly coupled to a portion of the applicator, connected to the applicator via hoses, and/or may be attached to any other appropriate method to provide fluid communication between the desired portions of an applicator and the one or more pressure sources. The one or more pressure sources may also be configured to provide a continuous flow of gas or a predetermined volume of gas depending on the desired application as elaborated on further below.

In some applications, it may be desirable for an applicator to be capable of fluidizing a powder contained therein in a number of different orientations. In general, the therapeutic powder is more easily fluidized when it is in contact with a porous portion of a chamber which gas flows through. Thus, it may be desirable to orient a chamber of an applicator such that the powder remains in contact with a porous portion of the chamber during use. To facilitate this positioning of the powder, in some embodiments it may be advantageous to angle a longitudinal axis of the chamber such that it may be angled relative to an axis passing through an outlet of the application which may be parallel with a flow out from the outlet. Angling the chamber relative to the outlet may help to maintain the powder in a desired portion of the chamber. Appropriate angles between the axis of the outlet and a longitudinal axis of the chamber may be greater than or equal to 15°, 20°, 30°, 45°, 60°, 70°, 90°, 120°, and/or any other appropriate angle. The angle of the longitudinal axis of the chamber relative to the axis of the outlet may also be less than or equal to 165°, 150°, 135°, 120°, 90°, 70°, 60°, and/or any other appropriate angle. Combinations of foregoing are contemplated including, for example, an angle between the longitudinal axis of the chamber and the axis of the outlet that is between or equal to 20° and 70°. While angling the longitudinal axis of the chamber relative to the axis of the outlet may facilitate effective fluidizing the powder within a chamber for different applicator orientations relative to a downward gravitational force, embodiments in which a longitudinal axis of a chamber and an axis passing through an associated outlet of an applicator are parallel and/or coaxial with one another are also contemplated as the disclosure is not so limited.

In some embodiments, an applicator may include a handle. The handle may be configured to rotate relative to another portion of the applicator to accommodate different holding positions and/or orientations. For example, the handle may be configured to rotate relative to a chamber of the applicator, such that the chamber may remain upright or otherwise oriented such that the powder remains in contact with a porous portion of the chamber during use. For example, a user may rotate the handle from a vertical orientation to a horizontal orientation, but may not change the orientation of the chamber relative to gravity. In some embodiments, the handle may be configured to rotate about a longitudinal axis of the applicator, which may enable the handle to "roll" relative to another portion of the applicator. For example, the handle may be configured to rotate about a rotation axis parallel to an axis passing through the outlet.

It should be appreciated that a handle of an applicator may be configured to rotate any suitable angle, as the present disclosure is not limited in this regard. For example, relative to an initial configuration, the handle may be configured to rotate an angle greater than or equal to −180°, −135°, −90°, −45°, −30°, −15°, 0°, 15°, 30°, 45°, 90°, 135°, and/or any other appropriate angle. The handle may be configured to rotate an angle less than or equal to −135°, −90°, −45°, −30°, −15°, 0°, 15°, 30°, 45°, 90°, 135°, 180°, and/or any other appropriate angle. Combinations of the foregoing are also contemplated. In some embodiments, a handle may be configured to rotate over 360°. In some embodiments, a handle may be configured to rotate in one or more directions without limitation.

In some embodiments, the handle may be configured to rotate in discrete increments. For example, the handle may be urged into preset angular positions separated by defined increments (e.g., increments of 5°, 10°, 15°, 30°, or any other suitable increment). Discrete rotation increments may be realized using detents, tab and slot arrangements, ratchet mechanisms, or any other suitable arrangement configured to enable discrete angular positioning. In some embodiments, the handle may be configured to rotate continuously. For example, the handle may rotate about a bushing or a bearing disposed between the handle and an outer housing of the applicator. In some embodiments in which the handle is configured to rotate continuously, the handle may be locked at any desired rotation angle. The handle may be locked using a friction collar, a thumb screw, a button, or any other suitable locking mechanism.

In some embodiments, a proximal portion of the applicator may rotate with the handle when the handle rotates relative to the chamber, and a distal portion of the applicator may remain stationary relative to the chamber. For example, a proximal portion may include a pressurized gas source (e.g., a bellows) and a handle, and a distal portion may include a chamber and an outlet. When the handle rotates relative to the chamber, the entire proximal portion may rotate relative to the entire distal portion. Accordingly, in such embodiments, the pressurized gas source may rotate with the handle when the handle rotates relative to the chamber. In such embodiments, a first portion of the overall flow path from the pressurized gas source to the outlet (e.g., the portion of the flow path within the proximal portion of the applicator) may rotate relative to a second portion of the overall flow path (e.g., the portion of the flow path within the distal portion of the applicator). The proximal and distal portions of the applicator (and/or the first and second portions of the overall flow path) may be rotatably coupled using any suitable coupling configured to allow relative rotation. For example, either one of the proximal portion or the distal portion of the applicator may include a flange, and the other of the proximal portion or the distal portion of the applicator may include a shelf and/or a ledge configured to engage the flange. The interface between the proximal and distal portions of the applicator may include a gasket, O-ring, or other component configured to seal the interface between the first and second portions of the overall flow path and prevent or minimize leakage of the pressurized gas.

In some embodiments, the handle may be the only component that rotates when the handle rotates relative to the chamber. For example, the pressurized gas source may be fixed relative to the chamber, such that the handle is configured to rotate relative to the pressurized gas source when the handle rotates relative to the chamber. In such embodiments, the overall flow path from the pressurized gas source to the outlet may not include portions that rotate relative to each other, as the handle may rotate about the overall flow path. Accordingly, such embodiments may not include a gasket, O-ring, or other sealing component.

An applicator may include any appropriate number, type, and/or arrangement of valves configured to control fluid flow. In some embodiments, an applicator may include one or more one-way valves (also called check valves or non-return valves) configured to prevent backflow of fluid into the outlet. For example, if an applicator includes a bellows as a pressurized gas source, expanding the bellows from a compressed configuration (e.g., after delivering a therapeutic powder) may be associated with generating a vacuum pressure. Such vacuum pressure may pull gas and/or liquid from the area surrounding the outlet back in through the outlet and into the applicator. Such backflow may be undesirable, in that the area surrounding the outlet may include moist, humid gas and/or liquid that may negatively affect the performance of the applicator if allowed inside the applicator. Accordingly, an applicator may include a first one-way valve configured to enable gas flow from the pressurized gas source to the outlet and configured to prevent fluid flow from the outlet to the pressurized gas source. The first one-way valve may be disposed at any suitable point along a flow path from the pressurized gas source to the outlet. For example, the first one-way valve may be disposed immediately downstream of the outlet of the pressurized gas source, or proximal to the outlet, although other suitable positions are contemplated. In some embodiments, an applicator may include a second one-way valve configured to enable gas to flow from the exterior environment into the applicator. For example, a second one-way valve may be configured to enable gas flow from the ambient air surrounding a bellows into the applicator to refill the bellows as it expands from a compressed configuration, but may be configured to prevent gas flow from the bellows to the ambient air when the bellows is compressed. The second one-way valve may be disposed at any suitable point along a flow path from the pressurized gas source to the outlet. The second one-way valve may be disposed at a location upstream of the first one-way valve in some embodiments.

It should be understood that an applicator may have any appropriately shaped chamber for containing a powder to be dispensed. However, in certain embodiments, a chamber of an applicator may have an elongated shape with a longitudinal axis extending along a length of the chamber. For example, the chamber may generally be cylindrical in shape with hemispherical ends. Such a shape may facilitate fluidization and dispensing of the powder through an outlet. For example, the shape may be absent of any sharp edges, corners, and the like which may disrupt the flow of gas and the fluidization of a powder within the chamber. However, embodiments in which sharp edges, corners, and other abrupt non-continuous design features are present along a flow path and/or within a chamber of an applicator are also contemplated as the disclosure is not so limited. For example a dog leg, or other sharp bend, may be present along a flow path connecting the various flow channels and/or chamber with one another.

In some embodiments, it may be desirable to dispense a predetermined amount of powder during actuation of a pressure source of an applicator. For example, actuation of a bellows, or other pressure source, in fluid communication with a porous chamber containing a powder may dispense a predetermined amount of powder from the applicator for each actuation cycle as detailed further below. In one embodiment, this may be accomplished by flowing a predetermined volume of gas at a desired pressure through the one or more flow paths of the applicator as might occur during a single actuation cycle of a bellows, a metered dispensing of gas from a pressurized source of gas, or any other appropriate method of dispensing a desired amount of gas at a desired pressure. This may permit substantially metered dispensing of powder from an applicator.

The applicators described herein may be used to dispense any appropriate type of powder as the disclosure is not limited in this fashion. However, as noted above, in some embodiments, the various embodiments of powder applicators described herein may be used to dispense a powder including one or more therapeutic compounds which may also be referred to as a therapeutic powder. Therapeutic compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. In a specific embodiment, the therapeutic compound may be a hemostatic agent. The amounts of therapeutic powder dispensed from an applicator may be selected such that an effective amount of the therapeutic compound may be dispensed at a desired location. When a therapeutic compound is present in a particular location in an “effective amount” it means a concentration of the therapeutic compound is greater than or equal to a trace amount and is sufficient for achieving a desired purpose, such as, for example, to permit detection of the therapeutic compound in a subject for diagnostic purposes, to treat a disease or condition in a subject, and/or enhance a treatment of a disease or condition in a subject. In some embodiments, an effective amount of a particular therapeutic compound is present in an amount sufficient to reduce or alleviate one or more conditions associated with a particular condition.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 shows a first embodiment of a therapeutic powder applicator 100. In this embodiment, the applicator is configured to be hand-held and operated using a bellows 120 configured to function as a first pressurized gas source. The bellows includes an internal compressible volume that is in fluid communication with a chamber 110 in which a powder may be contained. The chamber is formed at least partially from a porous material as indicated by the porous material 112 including a plurality of pores 114 forming the lower portion of the chamber. In the depicted embodiment, the chamber includes a second portion of non-porous material 116 that interfaces with and is connected to the porous material 112 at interface 115 to form the overall chamber, though instances in which the entire chamber is made from a porous material are also contemplated. As described earlier this interface may be selectively coupleable allowing the chamber to be opened to permit therapeutic powders to be added or removed from chamber 110 as desired. In other embodiments, porous material 112 and non-porous material 116 may be permanently connected at the interface 115 or the chamber may be a single unitary component.

As also shown in the figure, the internal volume of the bellows 120, or other appropriate pressure source, is fluidly connected to the internal volume of the chamber through the porous material of the chamber via a first gas conduit 122. In the depicted embodiment, the first gas conduit corresponds to one or more channels or gaps located between an exterior surface of the chamber and in interior surface of an outer housing 102 of the applicator as well as an associated connector 104 positioned between the bellows and the housing chamber. The connector may include an inlet 121 to the housing and the first flow conduit. In this embodiment, the non-porous material 116 of the chamber 110 may help to direct the first flow of gas around a proximal portion of the chamber 110 as it flows from the bellows 120 at a proximal end of applicator 100 towards a distal portion of the applicator where the porous portion of the chamber may be located distally from the non-porous portion of the chamber. Thus, the bellows, or other source of pressurized gas, may deliver a flow of gas to a distal portion of the chamber that may be proximate to an outlet from the chamber which in this case is an opening in fluid communication with a second conduit 132 located on a distal portion of the chamber. Alternatively, in some embodiments, the location to which a flow of gas from a gas source is delivered may be a distal portion of the chamber disposed on one or more sides of the chamber extending between the proximal and distal ends of the chamber such that the flow of gas flows into a bulk of the powder in the initial filled state rather than a proximal end of the chamber opposite the opening. Additionally, in some embodiments, and as depicted in the figure, the flow of gas into the volume surrounding the porous portion of the chamber may permit the flow of pressurized gas to enter the chamber along the entire porous portion of the chamber which in this case corresponds to the distal portion of the chamber proximate to the opening of the chamber.

In the above embodiment, the second conduit 132 is also in fluid communication with an outlet 130 of the applicator. This may help to avoid the flow of fluid into the chamber in a direction parallel to a direction of flow out of the chamber which may aid in fluidizing the powder contained therein. For example, depending on the particular arrangement, a flow of fluid from the bellows, or other gas source, may flow into the chamber in a direction that is angled relative to a longitudinal axis of the chamber and/or opening from the chamber. Appropriate angles may include, but are not limited to, angles between about 15° and about 180° (i.e. the opposite direction) such that the flow of gas into the chamber is not in the same direction as a flow of gas and entrained particles through an opening from the chamber, though angles both greater than and less than those noted above are contemplated as the disclosure is not so limited. However, it should also be understood that embodiments in which a direction of a flow of gas into a chamber and a direction of flow of gas and entrained particles out of a chamber are parallel to one another are also contemplated.

In the depicted embodiment, a longitudinal axis of the chamber 110 and an axis passing through an outlet 130 of the applicator are both substantially parallel and coaxially aligned with one another along the depicted axis 118. Additionally, the porous material 112 forms the bottom portion of the chamber 110 when the applicator is oriented with the outlet directed vertically downwards relative to a local gravitational field. When the applicator 100 is oriented in this vertical downwards orientation, or with a relatively small angular offset from vertical (e.g. less than 45 degrees from vertical), a majority of the therapeutic powder contained in the chamber may be disposed against the porous material 112 due to the gravity acting on the powder. Without wishing to be bound by theory, the primary mechanism by which fluidization is achieved is that the flowing gas disrupts the friction between the particles and the inner surfaces of chamber 110. As such, the effectiveness of fluidization may be dependent on what percentage of the powder is in contact with porous material 112 as a gas flows through the porous portions of a chamber. As such, the configuration shown in the first embodiment may be effective at fluidizing therapeutic powders when orientated vertically, or when offset by less than a predetermined angle from vertical (e.g., less than 45 degrees). However, it should be understood that operation of the depicted device is not limited to any particular range of angles as the various shapes, relative sizes, amount of porous material forming the chamber, and/or other appropriate operating parameters may be changed to provide a different range of operating angles for the operation of an applicator.

During operation, compressing the bellows 120 generates a first flow of gas which flows through first gas inlet 121 into the housing 102 of the applicator 100. From here, the first gas flow travels through the first gas conduit 122, which routes the gas around the chamber 110 from a proximal portion of the device near the bellows 120 to a distal portion of the device near outlet 130 where the porous material of the chamber is located. Upon reaching the distal portion of the device, the first flow of gas flows through plurality of pores 114 formed in the porous material 112 of chamber 110. After flowing through porous material 112, the first flow of gas fluidizes and entrains a therapeutic powder (not shown) located in the chamber 110 before flowing through the opening in the chamber into the second gas conduit 132. The entrained powder may then be dispensed from the outlet 130 with the flow of gas.

In embodiments where a bellows is used, the bellows may be configured such that the force applied to the bellows may impact the pressure and/or velocity of the gas delivered to the chamber or other portion of an applicator. This may in turn impact the fluidization and or distribution characteristics of the applicator. For example, applying a large force or rate of compression to the bellows may result in a higher pressure resulting in a higher volume of powder being fluidized and dispensed through the outlet with a smaller dispersion pattern over a smaller first area. In contrast, applying a smaller force or rate of compression to the bellows may result in a lower pressure resulting in a lower volume of powder being fluidized and dispensed through the outlet with a broad dispersion pattern over a second larger area. Of course similar functionalities may be obtained by controlling the pressure and/or flow rate of gases from any other appropriate pressure source as previously described.

Figure 2:
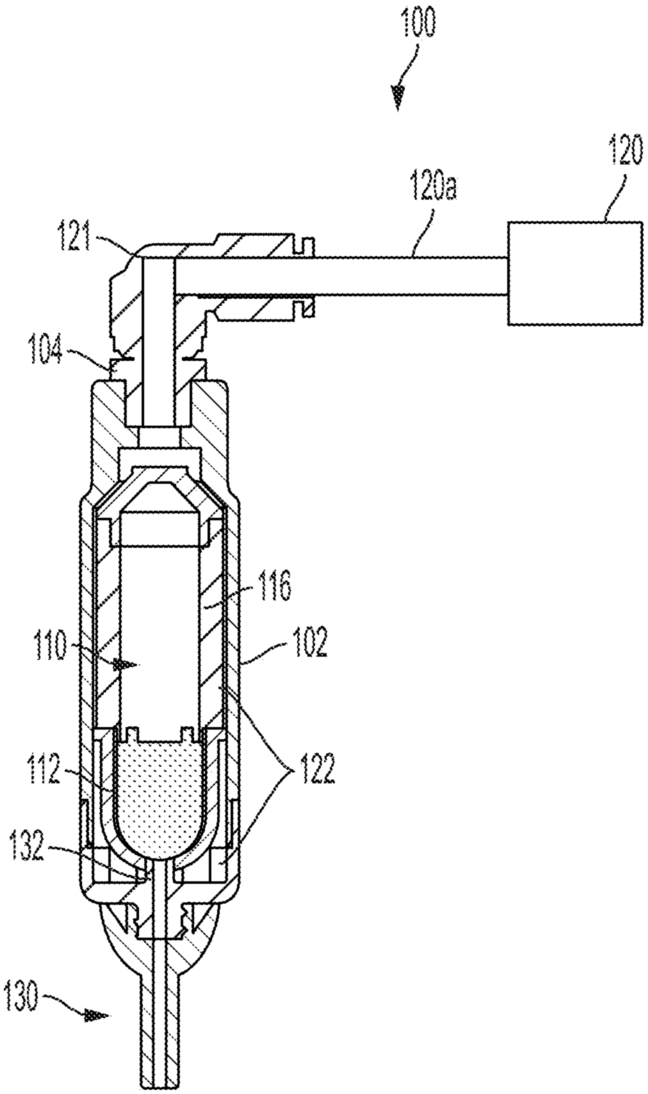
FIG. 2 is a cross sectional view of one embodiment of a powder applicator.

FIG. 2 shows a second embodiment of an applicator 100. In this embodiment, the applicator 100 is similar to the embodiment described relative FIG. 1. However, the applicator is now configured to operate using gas supplied by a pressurized gas source 120 other than a bellows. For example, an operating/medical room gas supply or a gas canister may be fluidly connected to the applicator by an associated tubing 120*a* or other appropriate connection in fluid communication with the first gas inlet 121 of the applicator. In this embodiment, the first gas inlet 121 includes a 90 degree elbow, although in other embodiments any angular offset, or a straight connection, may be used. The tubing may be attached to the first gas inlet by any suitable connection including, but not limited to a quick connect fitting, a threaded connection, adhesives, a compression fitting, and/or any other appropriate type of connection. In alternate embodiments, a suitably sized canister could be attached to a housing 102 of the applicator 100 and fluidly connected to the first gas inlet 121. As with the embodiment shown in FIG. 1, the gas flow flows through the first gas conduit 122 from a proximal portion of the device near the first gas inlet 121 towards a distal portion of the device near outlet 130. At this point, the gas may flow through the porous material 112 of chamber 110 where it fluidizes and entrains a therapeutic powder (not shown) before carrying the powder through the second gas conduit 132 to dispense the powder through the outlet 130.

Figure 3:
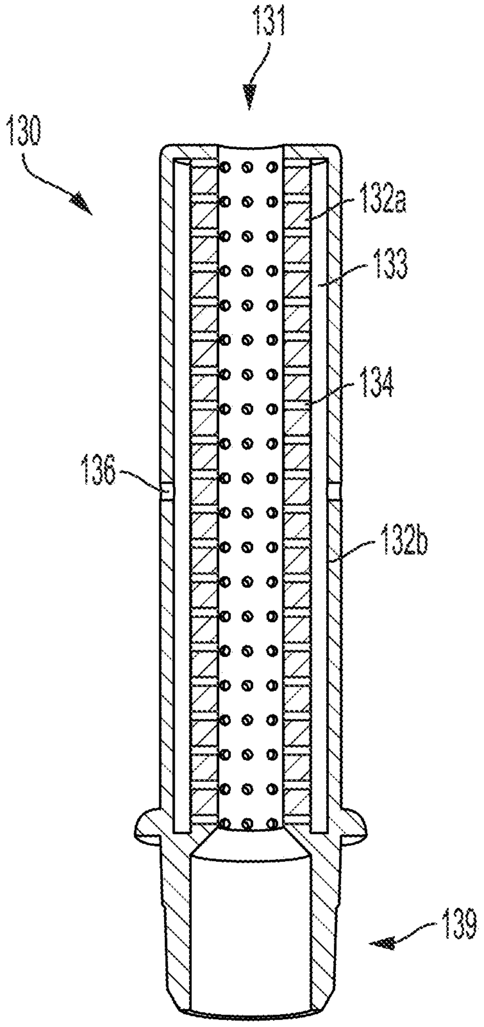
FIG. 3 is a cross sectional view of one embodiment of a powder applicator nozzle.

FIG. 3 shows an isolated view of one embodiment of an outlet 130 of an applicator. In this embodiment, the outlet 130 includes a first interior wall 132*a* formed from a porous material that defines at least a portion of a channel 131 extending through the nozzle. The interior wall may be spaced from an second wall 132*b* of the nozzle that is disposed radially outward from the interior wall such that an interior volume 133 may be formed between the first and second walls. The walls are depicted as cylindrical tubes. However, any appropriate shape of the walls and corresponding volume may be used. In the depicted embodiment, the second wall may be made from a non-porous material and the first interior wall may include a plurality of pores 134 formed in the wall such that the interior volume disposed between the walls is in fluid communication with the channel extending through the nozzle through the plurality of holes formed in the first interior wall. It should be understood that any porous material may be used to form the interior wall including holes formed in a solid material, a porous membrane material, or any other appropriate porous material. The nozzle may include an inlet 136 to the interior volume located at any point between the first and second walls, with some embodiments positioned distally and some proximally from the outlet 131.

During operation, a flow of gas that is separate from a primary flow of gas through the channel 131 of the nozzle 130 may be supplied from a pressurized gas source through the inlet 136 into the interior volume 133 between the first and second walls 132*a* and 132*b*. The pressurized gas source may either be the same or different from a pressurized gas source used to provide a primary flow of gas through the applicator nozzle. In either case, the gas may be at a larger pressure relative to the primary flow of gas through the channel of the nozzle such that the gas flows from the interior volume through the pores of the first interior wall into the channel. This flow of gas into the channel of the nozzle through the interior wall forming the channel may help to retain powder entrained in the flow of gas through the nozzle which may help avoid clogging of an applicator. Of course, while a particular nozzle design has been described in relation to the figure, it should be understood that any appropriate type of nozzle may be used with the various embodiments of applicators described herein including nozzles without the depicted construction.

Figure 4A:
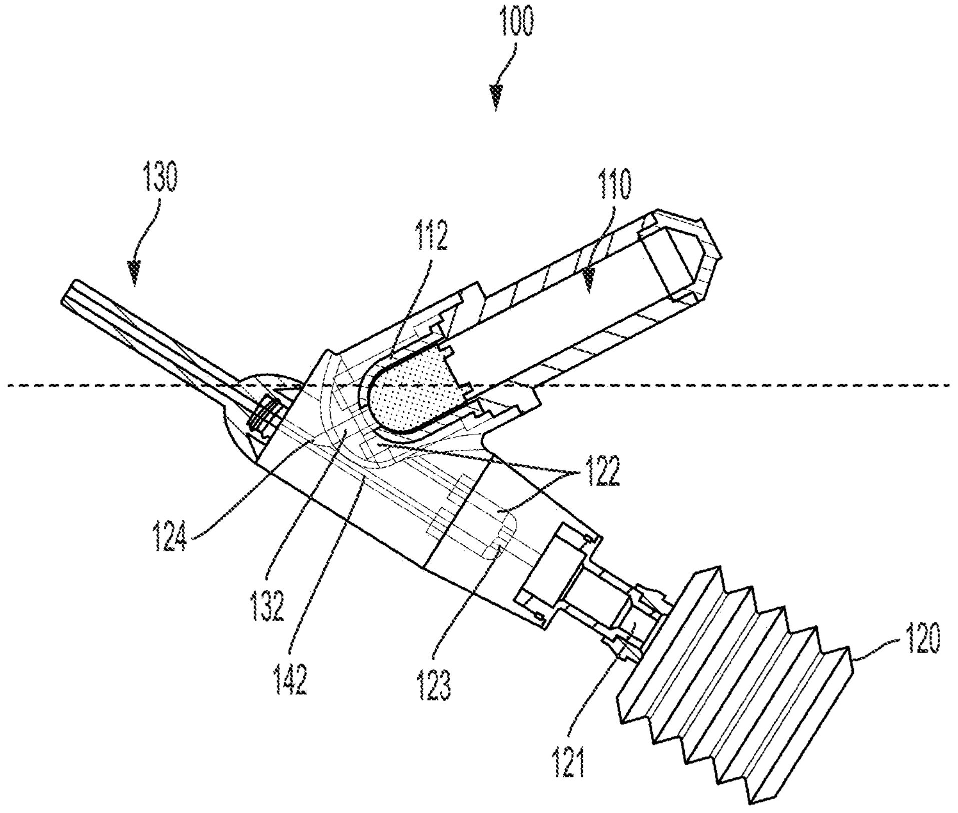
FIGS. 4A-4C is a cross sectional view of one embodiment of a powder applicator including two flow paths in different orientations.
Figure 4B:
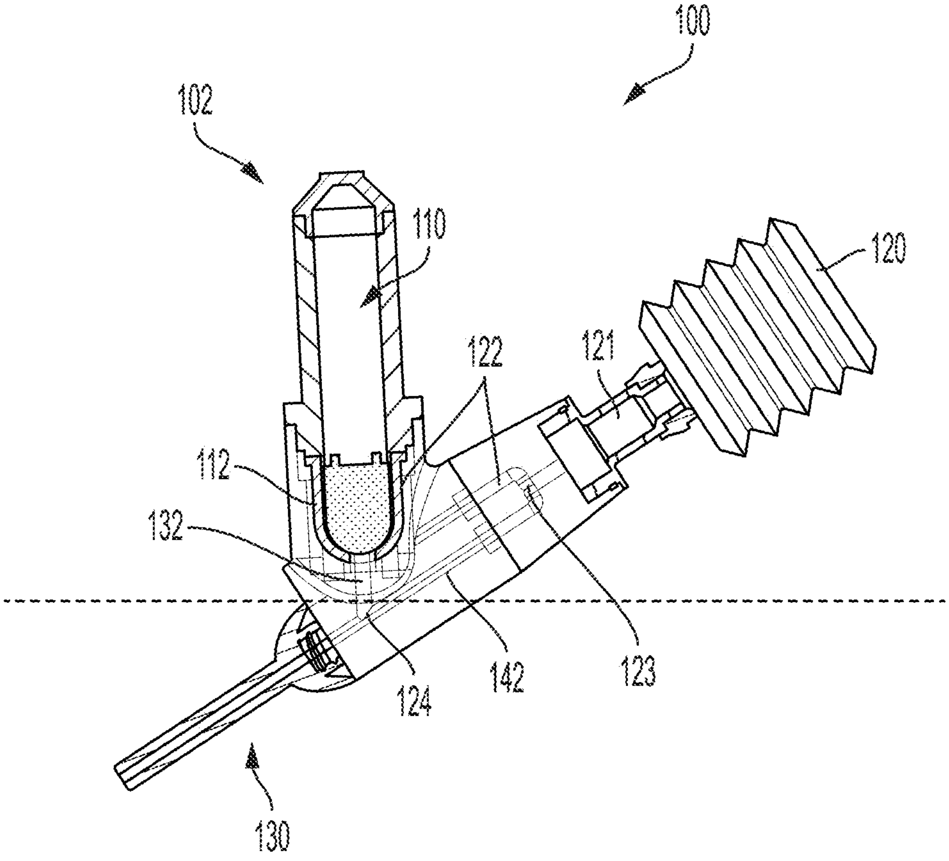
Figure 4C:
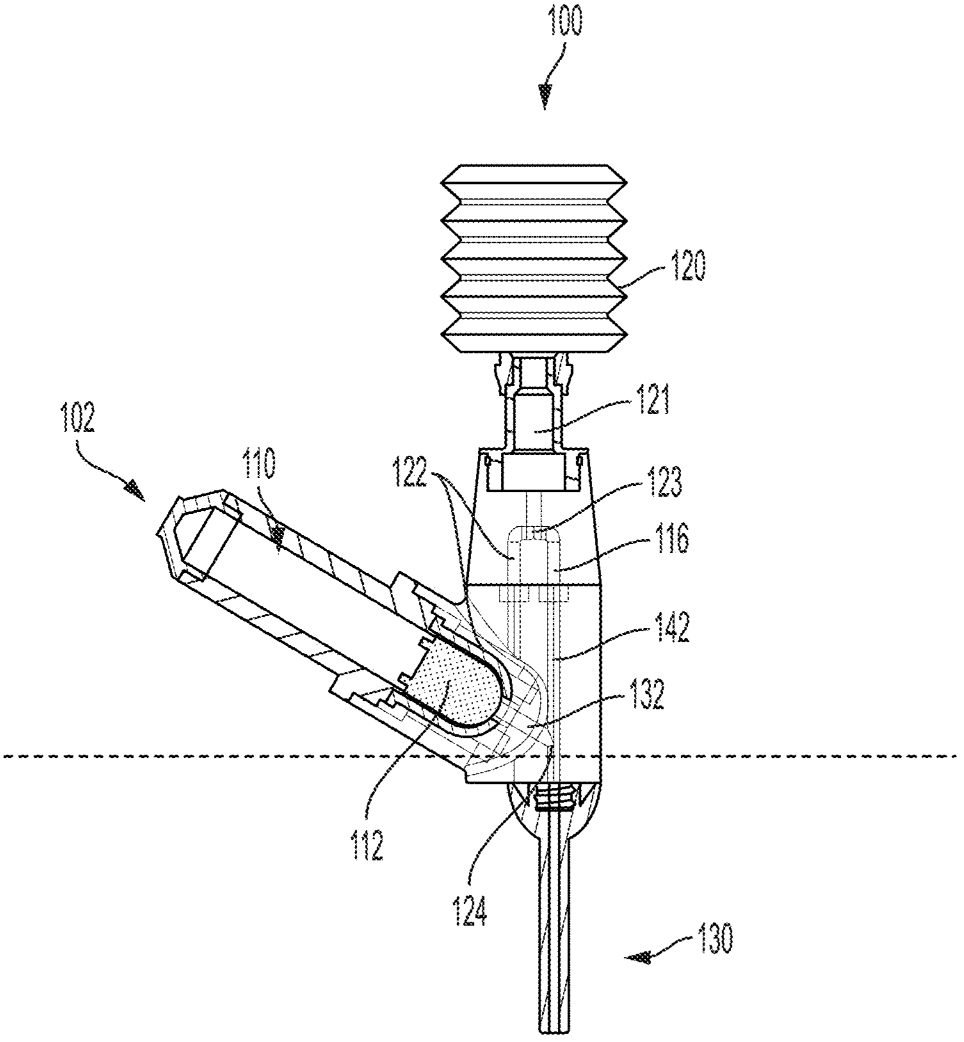

FIGS. 4A through 4C show a third embodiment of a therapeutic powder applicator 100. Most notably, the third embodiment is configured to include a second gas flow path and includes an angular offset between a longitudinal axis of chamber 110 and an axis passing through an outlet 130 of the applicator. Bellows 120 is configured to be the first pressurized gas source in this embodiment. Similar to the above embodiments, the bellows, or other pressure source, is in fluid communication with a porous portion of a chamber 110 of the applicator including a powder, not depicted, through a first gas inlet 121 in fluid communication with a first conduit that is in fluid communication with a volume surrounding a porous material 112 forming a portion of the chamber. Similar to the above embodiments, the first conduit may deliver a flow of the pressurized gas to a location that is proximate to an opening in the chamber through which the gas and entrained particles may flow. In the depicted embodiment, an outlet from the first conduit is oriented towards the porous portion of the chamber at an angle that is different from an angle of an axis extending through an opening 132 formed in the chamber. The bellows may also be in fluid communication with a second flow path in the form of a second conduit 142 that bypasses the chamber. A flow path connecting the bellows to the first and second conduits through the gas inlet may split at a first junction 123. These separate first and second flow paths may be recombined at a second junction 124 located downstream from chamber and second conduit prior to passing through the outlet of the applicator.

During operation, compressing bellows the 120 generates a first flow of gas which flows through the gas inlet 121 into the interior of the applicator 100. Upon entering the applicator, the first gas flow encounters a first junction 123 where the gas flow splits into two distinct streams. The first gas flow enters first gas conduit 122, where it flows through the porous material 112 of the chamber 110 where the gas fluidizes and entrains a powder contained in the chamber as described above. The separate second gas flow enters into and flows along the second gas conduit 142 to the second junction 124 such that the second gas flow bypasses, i.e. does not flow through, the chamber including the powder. Correspondingly, powder entrained in the first flow of gas exiting through an opening 132 of the chamber may also flow into the second junction 124 where the entrained powder and first flow of gas is combined with the second flow of gas. Depending on the relative velocities of the two flows of gas, the second gas flow may aerosolize the entrained powder in the combined flow of gas before flowing out through the outlet 130.

As noted above, FIGS. 4A-4C also depict a chamber 110 with a longitudinal axis that is angled relative to an axis extending through an outlet 130 of the applicator 100. In the depicted embodiment, the angle between the longitudinal axis of the chamber and the outlet is about 45°, though other appropriate angles may also be used. The figures include a dashed line, representing a horizontal plane perpendicular to a direction of gravity. FIG. 4A shows the applicator outlet tilted upwards relative to the horizontal plane by an angle of approximately 45 degrees, FIG. 4B shows the applicator with the outlet tilted downwards relative to the horizontal plane by an angle of approximately 45 degrees, and FIG. 4C shows the applicator outlet oriented vertically downwards. Due to the chamber's longitudinal axis being angled relative to the axis passing through the applicator outlet, in each of these three orientations, the portion of a chamber made from a porous material 112 may be located on a most vertically downwards portion of the chamber. Accordingly, gravity acting on a powder contained within the chamber may maintain a large portion of the powder into contact with porous portion of the chamber. As described above, maintaining the powder in contact with the porous portion of the chamber through which a gas may flow may help to ensure adequate fluidization of the powder contained therein. Thus, embodiments, like those shown in FIGS. 4A through 4C in which the longitudinal axis of chamber 110 is angled relative to the axis of outlet 130, may enable a wider range of effective operating orientations of an applicator as compared to applicators in which the longitudinal axis of a chamber is aligned with an axis extending through an outlet of the applicator.

Figure 5:
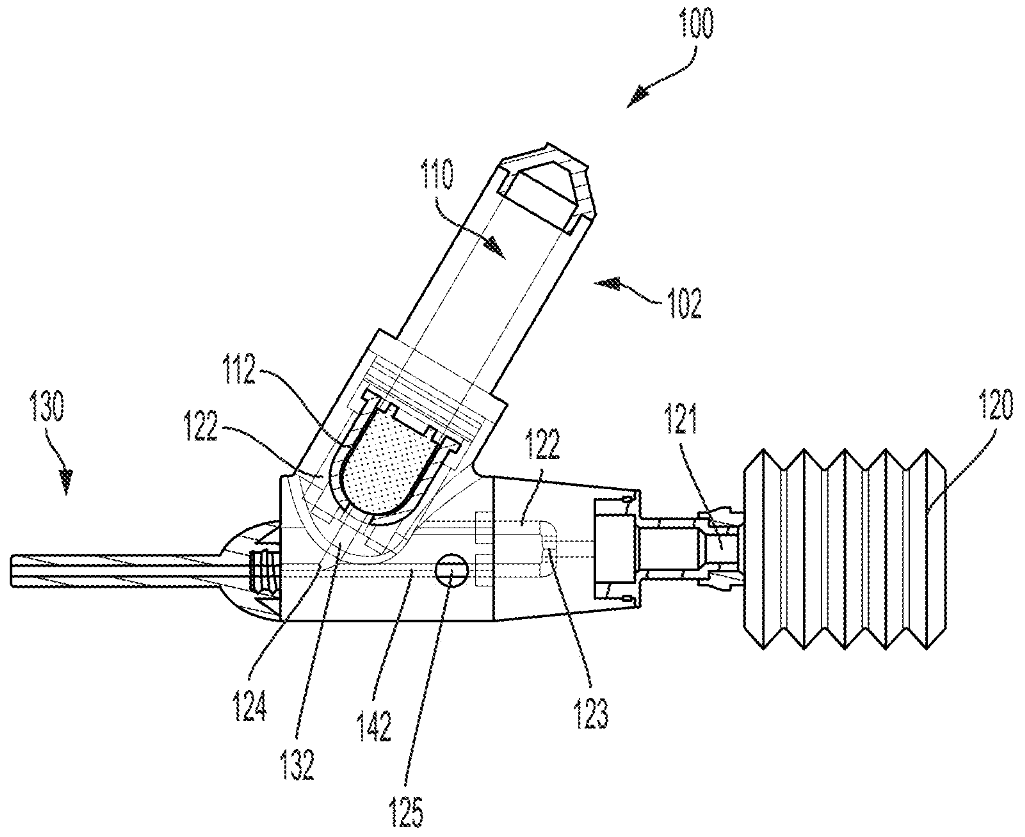
FIG. 5 is a cross sectional view of one embodiment of a powder applicator including two flow paths and a valve.

FIG. 5 shows another embodiment of a powder applicator 100. This is similar to the embodiment described above relative to FIGS. 4A-4C. However, a variable fluid restriction, such as a valve 125, may be disposed along the second gas conduit 142 between the first junction 123 and the second junction 124. This valve may be configured to adjust the relative flow resistances, and thus the flow rates of gas through, the first conduit 122 and second conduit 142. Depending on the desired operation the variable flow resistance may be operated to provide a variable flow resistance through the second conduit that bypasses the chamber that is less than, equal to, and/or greater than a flow resistance through the first conduit and associated chamber. Further, in some instances, the variable flow resistance may be used to close the second conduit in which case, operation of the applicator may be similar to that described in the prior embodiments including a single flow path. By appropriately varying the relative flow resistances of the different flow paths through an applicator, it may be possible to vary the amount, velocity and/or spread of the dispensed powders. For example, and without wishing to be bound by theory, a small coverage area and higher powder dispense rate may be achieved by using a lower pressure in the second flow path that bypasses the powder chamber which may have a relatively higher pressure in one mode of operation. In another mode of operation, a larger coverage area and lower powder dispense rate may be achieved by using a higher pressure in the second flow path relative to a lower pressure in the chamber.

In the above embodiment, a valve 125 disposed on the second flow path that bypasses the chamber 110 has been depicted. However, embodiments in which a valve, or other flow restriction, is disposed on either one, or both, of the first and second flow paths are also contemplated as the disclosure is not limited to how the relative flow resistances between these two flow paths are controlled. Additionally, it should be understood that the valve, or other appropriate variable flow resistance, may be operated either manually and/or through electrical control as the disclosure is not limited to the specific method for controlling a variable flow resistance.

Figure 6:
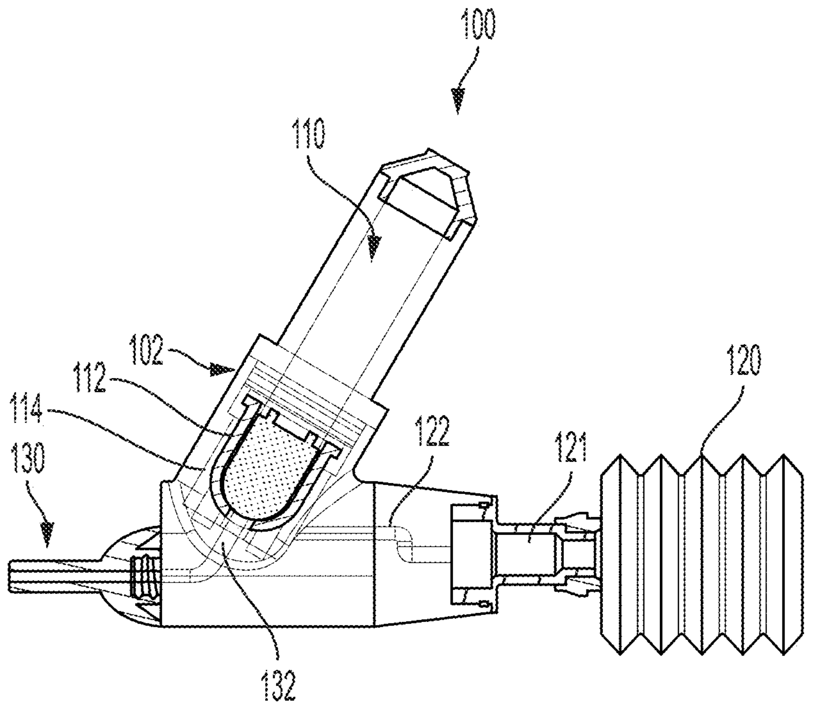
FIG. 6 is a cross sectional view of one embodiment of a powder applicator.

FIG. 6 shows yet another embodiment of a powder applicator 100 similar to those described above. This embodiment includes only a single flow path and a chamber 110 with a longitudinal axis that is angled relative to an axis passing through an outlet 130 of the applicator as described above. Additionally, as best seen in FIG. 6, in some embodiments, a downstream opening of the first conduit 122 into an interior of the housing including the chamber may be radially offset from an opening 132 formed in the chamber while still directing a flow of gas towards a distal portion of the chamber disposed between an opening from the chamber and a proximal end of the chamber located opposite the opening. Again, the first conduit may also direct the flow of gas into a volume surrounding the distal porous portion of the chamber. The opening of the conduit may also be directed in a direction that is angled relative to the longitudinal axis passing through the opening of the chamber and/or the chamber itself. Again, this may help to avoid a flow of gas exiting the conduit and flowing directly into the opening of the chamber without fluidizing the powder contained within the chamber. In addition to the above, the depicted embodiment may also be capable of providing fine control over the amount and spread of powder dispensed from the applicator. Specifically, compressing the bellows 120 at a relatively slow rate may allow for focused dispensing of a larger amount of powder over a smaller area as compared to dispensing a smaller amount of powder over a larger area when the bellows are compressed at a relatively faster rate.

Figure 7:
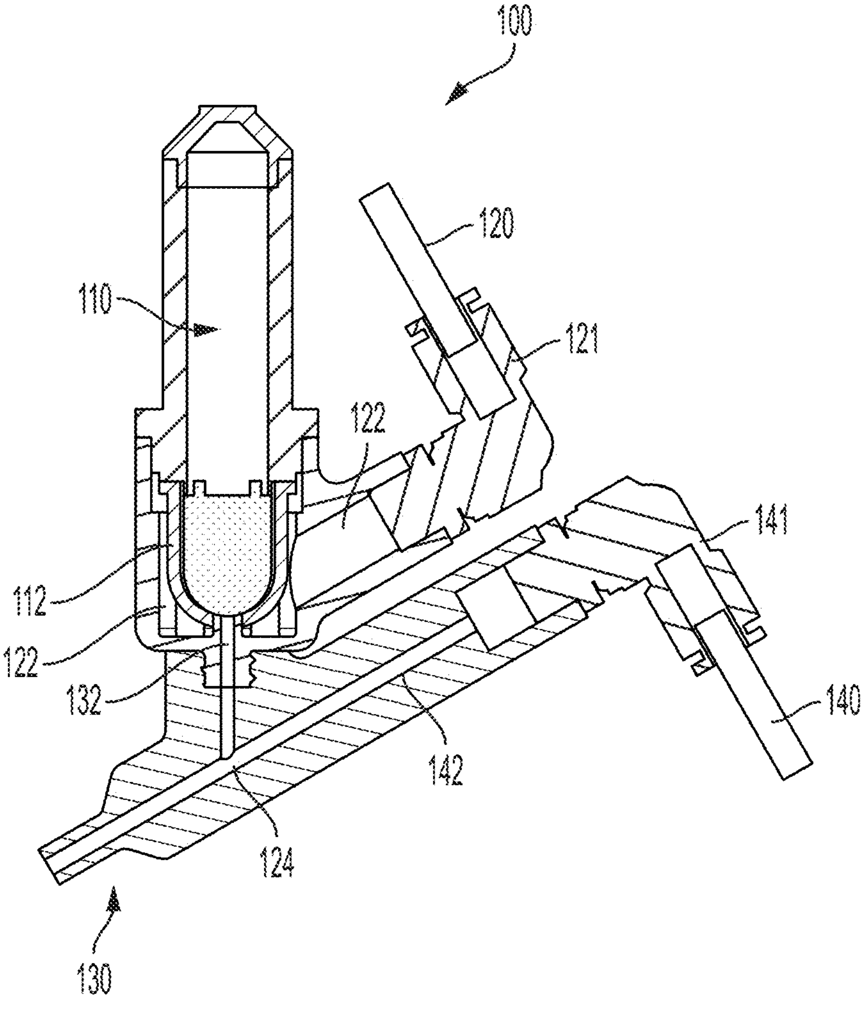
FIG. 7 is a cross sectional view of one embodiment of a powder applicator with two gas sources.

FIG. 7 shows another embodiment of a powder applicator 100 similar to that of FIGS. 4A-4C. In this embodiment, the applicator 100 is configured to receive a first flow of gas from a first pressurized gas source and a second flow of gas from a second pressurized gas source that is separate from the first pressurized gas source. In this embodiment, the first pressurized gas source 120 and second pressurized gas source 140, which may be gas feeds or canisters as described above, are fed into the applicator 100 at a first gas inlet 121 and a second gas inlet 141. Upon entering the applicator 100, the first gas flow flows through a first gas conduit 122, through a porous material 112 forming at least a portion of a chamber 110 where the first flow of gas fluidizes and entrains a powder contained in the chamber (not shown). The entrained powder then flows through an opening 132 formed in the chamber to a second junction 124. The separate second flow of gas flows through the second conduit 142 to junction 124. At junction 124, the first flow of gas with the entrained powder and second flow of gas are combined to form a combined flow of gas and entrained powder that then flows through the outlet 130. Similar to the use of variable flow restrictions in either one or both flow paths of a device, the pressurized gas sources may be operated to adjust an amount of gas flowing through the various flow paths to adjust how powder is dispensed from an applicator as described above. It should be understood that the first and second pressurized gas sources may be configured to operate independently, such that no gas may flow, only the first flow of gas may flow to chamber 110, only the second flow of gas may flow to outlet 120, or both the first and second flows of gas may flow. However, embodiments in which the first and second pressurized gas sources are operated in conjunction with one another are also contemplated.

Figure 9A:
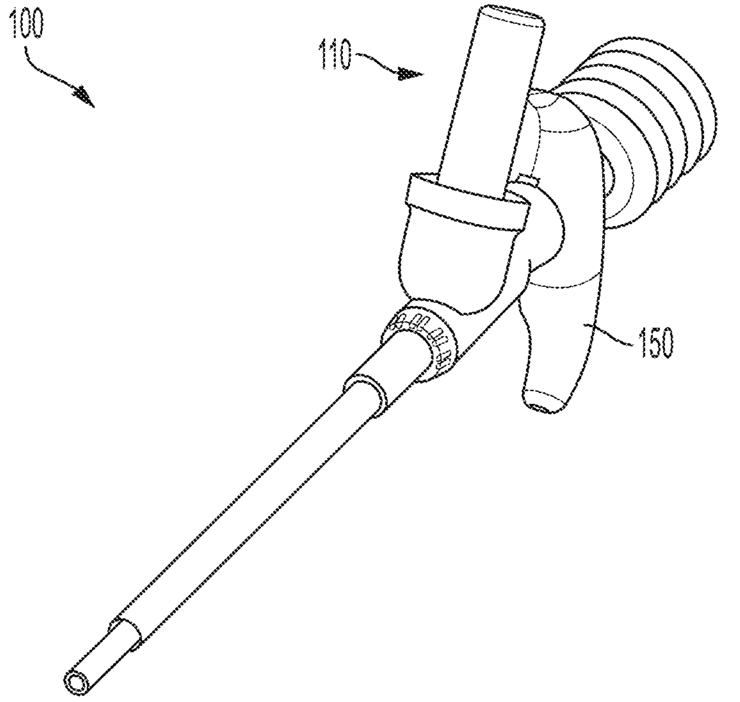
FIG. 9A is a perspective view of one embodiment of a powder applicator with a handle in a first position.
Figure 9B:
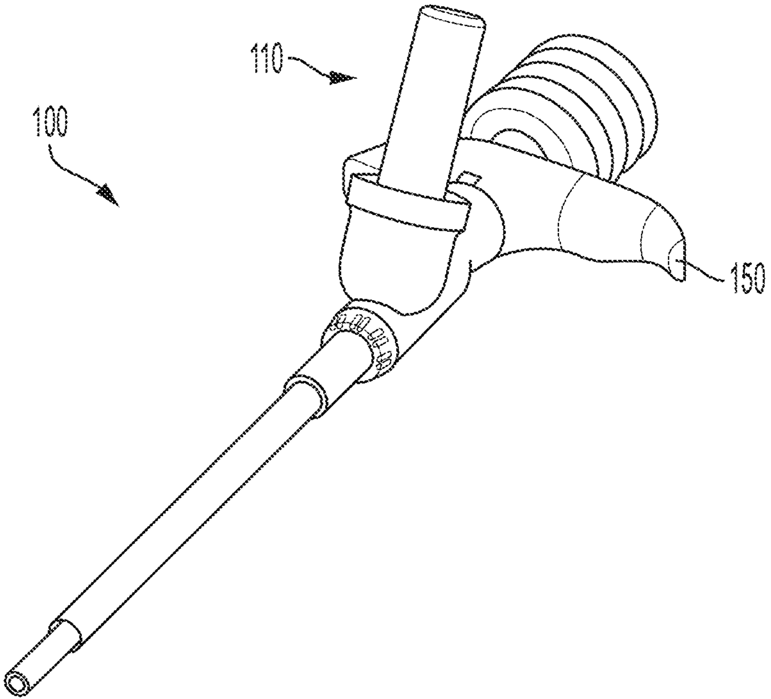
FIG. 9B is a perspective view the powder applicator of FIG. 9B with the handle in a second position.

FIGS. 9A and 9B show one embodiment of a powder applicator 100 with a rotatable handle 150 in different positions. In the configuration of FIG. 9A, the handle 150 is in a vertical orientation relative to the chamber 110. In the configuration of FIG. 9B, the handle 150 is in a horizontal orientation relative to the chamber 110. As explained above, rotating the handle 150 relative to the chamber 110 may enable a user to adjust holding positions (e.g., to gain better access to a target delivery site) while keeping the chamber in an orientation in which the powder remains in contact with a porous portion of the chamber. Although only two different handle positions are depicted in FIGS. 9A and 9B, it should be appreciated that a handle may be configured to rotate to any suitable angle, as described above.

Figure 10:
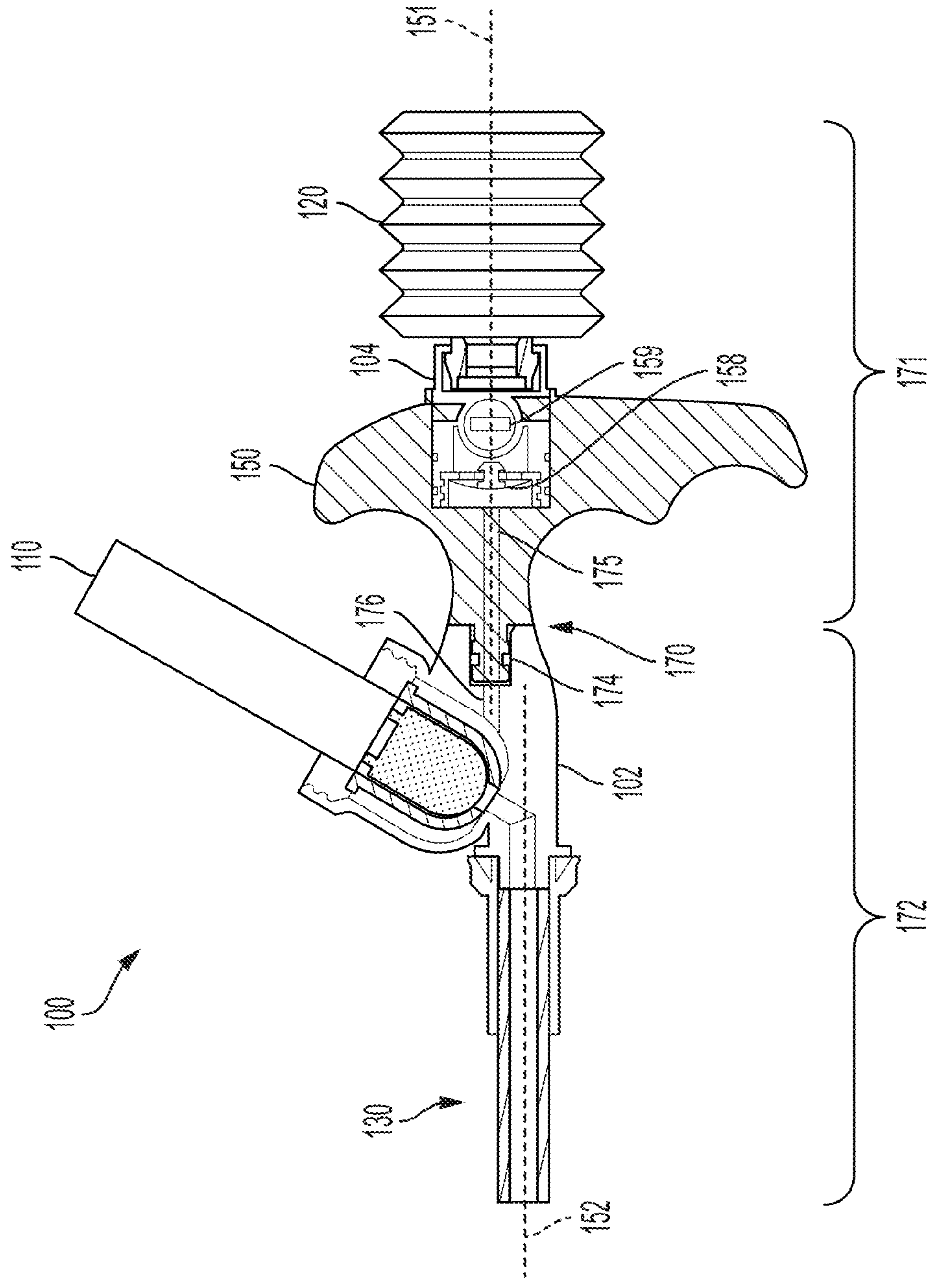
FIG. 10 is a cross sectional view of one embodiment of a powder applicator with a rotatable handle.

FIG. 10 shows one embodiment of a powder applicator 100 with a rotatable handle 150. In this embodiment, a proximal portion 171 of the applicator is configured to rotate relative to a distal portion 172 of the applicator. The proximal portion 171 includes a bellows 120 (or other suitable pressurized gas source), the handle 150, and a first portion 175 of the overall flow path from the bellows 120 to the outlet 130. The distal portion 172 includes a chamber 110, the outlet 130, and a second portion 176 of the overall flow path. The handle 150 (and the remainder of the proximal portion 171) may be configured to rotate about a rotation axis 151 parallel to an axis 152 passing through the outlet 130. The proximal portion 171 and the distal portion 172 may be rotatably coupled at an interface 170, which may include a sealing component 174 such as a gasket or an O-ring, as described in greater detail above.

While the handle depicted in FIGS. 9 and 10 has been illustrated as being used with an applicator with a chamber at a particular angle and a single flow path connecting the bellows to the outlet, it should be understood that the depicted handle may be used with any of the embodiments of an applicator disclosed herein as the disclosure is not so limited.

Also shown in FIG. 10 are valves configured to prevent backflow, including a first one-way valve 158 and a second one-way valve 159. As described above, the first one-way valve 158 may be configured to enable gas flow from the bellows 120 to the outlet 130 and may be configured to prevent fluid flow from the outlet 130 to the bellows 120. In the embodiment of FIG. 10, the first one-way valve 158 is disposed immediately downstream of the outlet of the bellows 120. In other embodiments, the first one-way valve may be disposed at another position, such as proximal to an outlet, as discussed above. The second one-way valve 159 may be configured to enable gas flow from the ambient air surrounding the bellows 120 into the applicator 100, but may be configured to prevent gas flow from the bellows 120 to the ambient air when the bellows 120 is compressed. In the embodiment of FIG. 10, the second one-way valve 159 is disposed adjacent to the first one-way valve 158 and angled relative to the first one-way valve 158. However, it should be appreciated that the second one-way valve may be disposed in a plurality of suitable locations and at a plurality of suitable orientations. Additionally, it should be appreciated that an applicator may include any suitable number of valves (such as the first one-way valve 158 and the second one-way valve 159) regardless of whether or not the applicator includes a handle.

Figure 11:
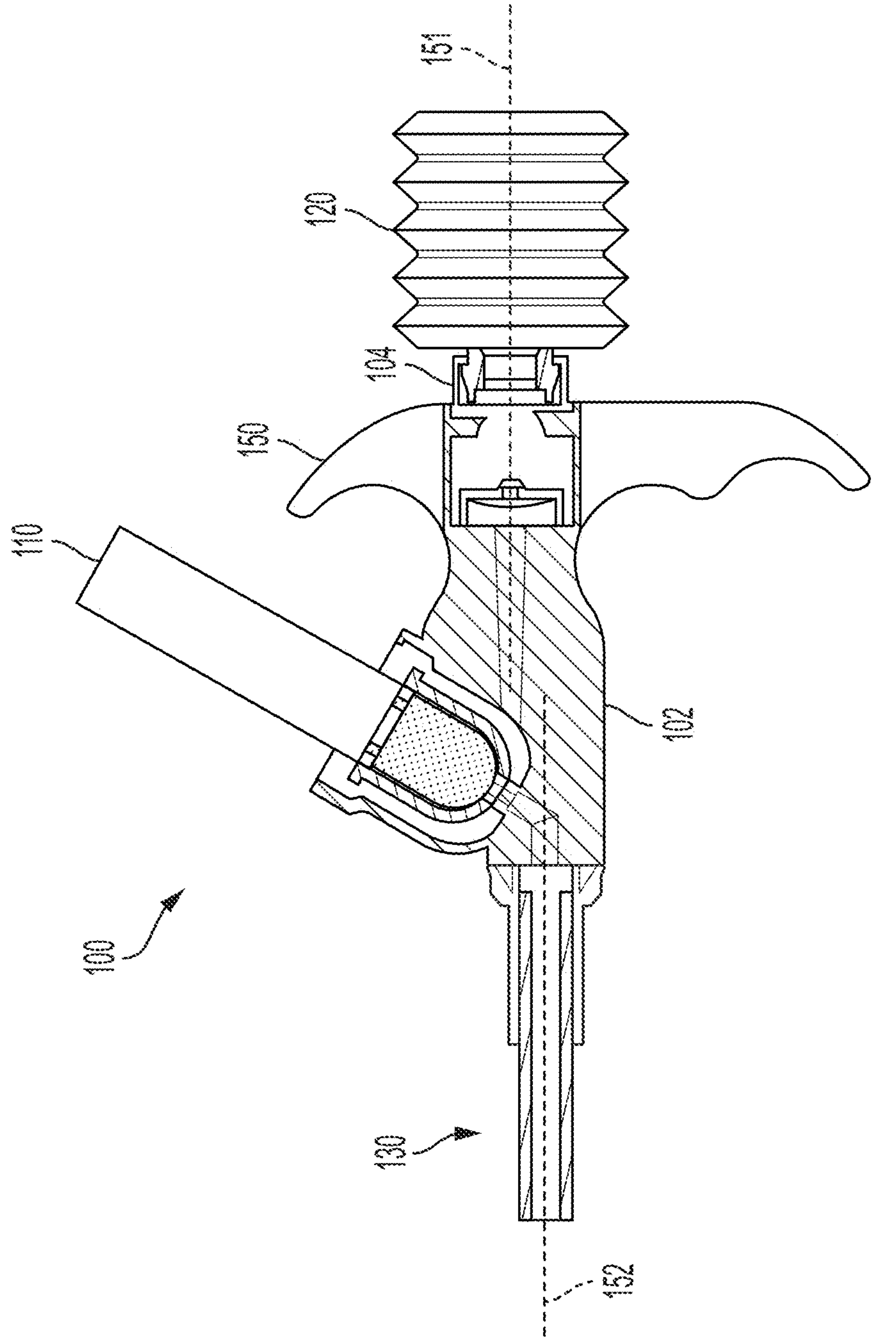
FIG. 11 is a cross sectional view of another embodiment of a powder applicator with a rotatable handle.

FIG. 11 shows another embodiment of an applicator 100 with a rotatable handle 150. In this embodiment, the handle 150 rotates relative to an outer housing 102 of the applicator 100 while the other components of the applicator 100 (e.g., the bellows 120, the chamber 110, and the outlet 130) remain stationary. As such, the handle 150 may be configured to rotate relative to both the chamber 110 and the bellows 120.

The handle 150 may be configured to rotate about a rotation axis 151 parallel to an axis 152 passing through the outlet 130.

Figure 12B:
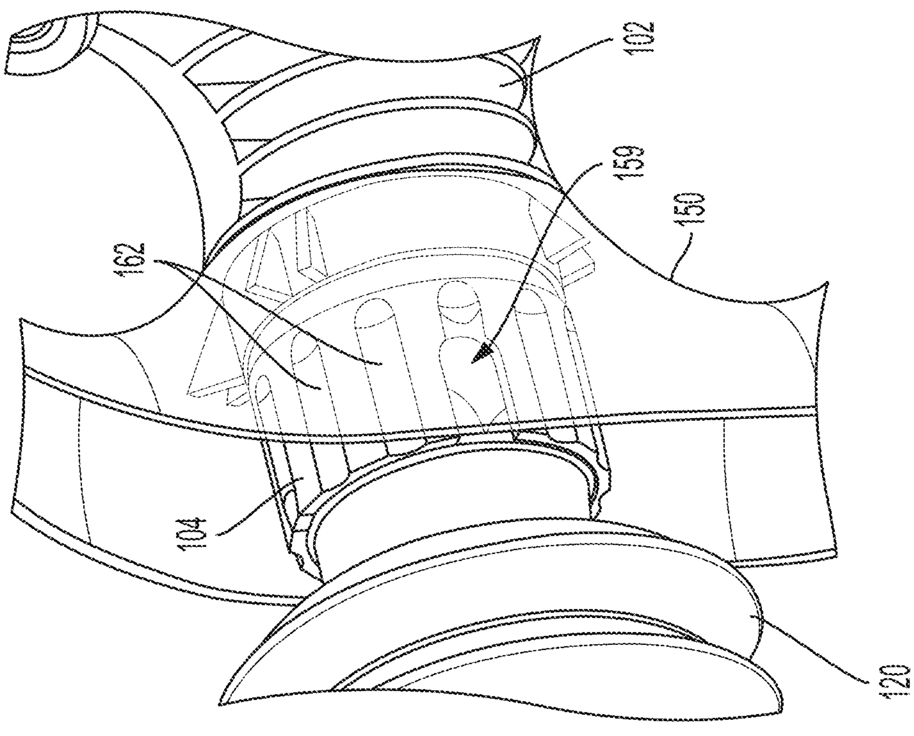
FIG. 12B is a perspective view of one embodiment of a powder applicator with a valve.
Figure 12A:
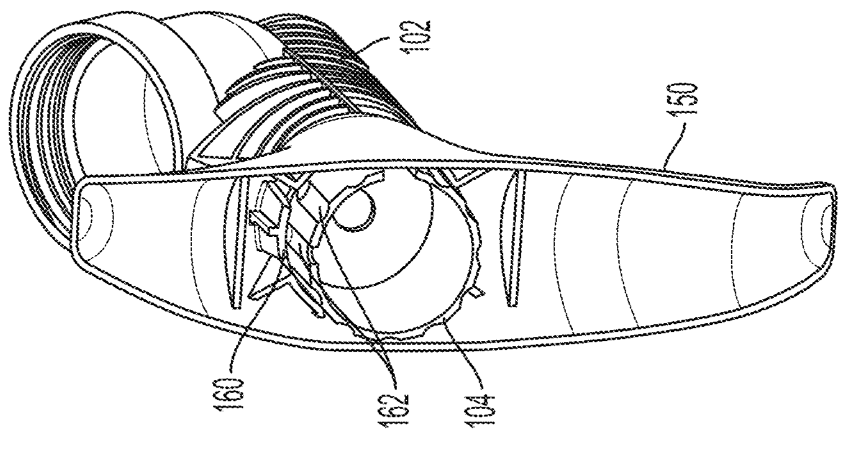
FIG. 12A is a perspective view of one embodiment of a powder applicator handle.

FIGS. 12A and 12B show details of one embodiment of an interface between a handle 150 and an applicator. The handle 150 includes a protrusion 160 configured to be received by any one of multiple recessions 162. The recessions 162 may be associated with any suitable portion of the applicator 100, such as an outer housing 102, but in the embodiment of FIG. 12A, the recessions 162 are associated with a connector 104 positioned between the bellows 120 and the outer housing 102. When the handle 150 is rotated, the protrusion 160 is urged into one of the recessions 162 such that the handle 150 is locked at a discrete angular position.

While the handle depicted in FIG. 11 has been illustrated as being used with an applicator with a chamber at a particular angle and a single flow path connecting the bellows to the outlet, it should be understood that the depicted handle may be used with any of the embodiments of an applicator disclosed herein as the disclosure is not so limited.

FIG. 12B additionally shows a one-way valve that will be referred to as the second one-way valve 159 (for consistency with the above description). The second one-way valve 159 may be configured to enable gas flow from the ambient air surrounding the bellows 120 into the applicator 100 (e.g., when the bellows is expanded), but may be configured to prevent gas flow from the bellows 120 to the ambient air (e.g., when the bellows 120 is compressed). In the embodiment of FIG. 12B, the second one-way valve 159 is positioned between the bellows 120 and the outer housing 102, and is oriented perpendicular to the flow path between the bellows 120 and the outer housing 102. However, it should be appreciated that in other embodiments, the second one-way valve may be at other positions and/or orientations, as the disclosure is not limited in this regard.

Example: Variable Operation of a Powder Applicator

Figure 8:
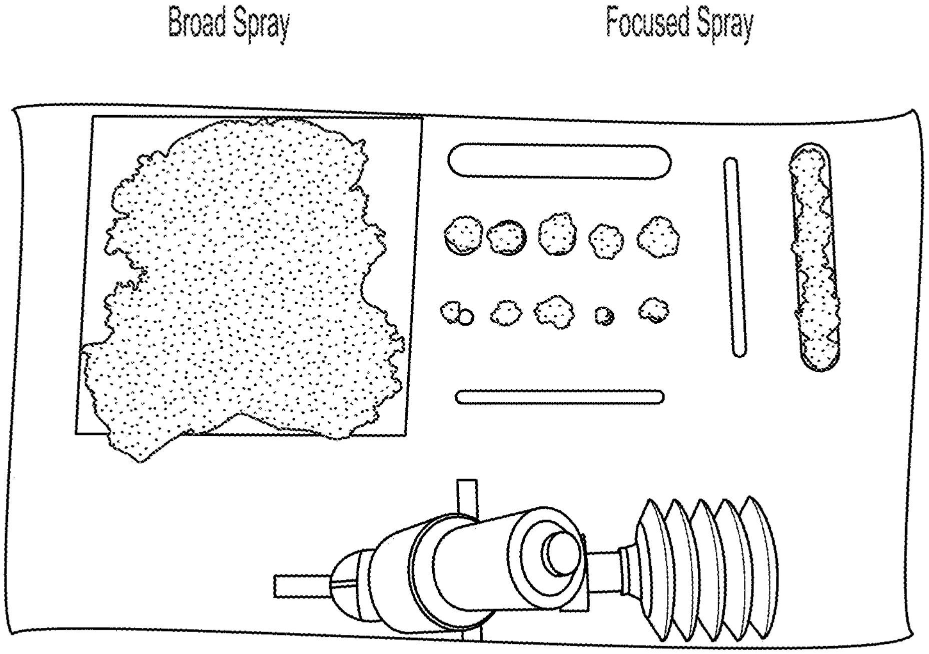
FIG. 8 is a photograph of one embodiment of a powder applicator used to apply powder to different sized areas.

FIG. 8 shows a representative figure of different powder distribution patterns that are achievable using a therapeutic powder applicator similar to that shown in FIG. 6. The left shows a broad, diffuse distribution pattern. The right shows a focused distribution pattern over a smaller area. These different distributions were obtained by varying the rate of depressing the bellows of the applicator as described above.

Example: Powder Flowability Characteristics:

Dry powders with a Hausner ratios between about 1.08 and 1.39 were characterized and evaluated with regards to flowability. Based on the performed testing, and without wishing to be bound by theory, it was found that lower Basic Flowability Energy (BFE), lower Aerated Energy (AE), higher Aeration Ratio (i.e. less cohesive due to a higher sensitivity to aeration), lower wall friction angle (WFA) (due to lower sliding resistance between the powder and wall), and a lower Compressibility Percent were associated with improved flowability of the powder.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A therapeutic powder applicator comprising:

a chamber configured to contain a therapeutic powder, wherein at least a distal portion of the chamber includes a porous membrane comprising a plurality of pores, and wherein the chamber is at least partially formed from the porous membrane such that the porous membrane defines a volume of the chamber and is configured to support the therapeutic powder during operation;

a first pressurized gas source in fluid communication with the chamber through the plurality of pores of the distal portion of the chamber; and an outlet in fluid communication with the chamber, wherein the distal portion of the chamber is located adjacent to the outlet, wherein the first pressurized gas source and the chamber are configured such that a first flow of gas from the first pressurized gas source flows around at least a proximal portion of the chamber before entering the plurality of pores of the distal portion of the chamber to entrain the therapeutic powder in the first flow of gas, and wherein the therapeutic powder applicator is configured to be a handheld applicator and the outlet is configured to deliver the therapeutic powder to a target area of a subject.

2. The therapeutic powder applicator of claim 1, further comprising the therapeutic powder disposed in the chamber.

3. The therapeutic powder applicator of claim 2, wherein the therapeutic powder is a hemostatic powder.

4. The therapeutic powder applicator of claim 1, wherein the pressurized gas source and the chamber are configured such that the entrained therapeutic powder flows through the outlet.

5. The therapeutic powder applicator of claim 4, wherein the first pressurized gas source and the outlet are configured such that a second flow of gas from the first pressurized gas source flows through the outlet without flowing through the chamber.

6. The therapeutic powder applicator of claim 5, wherein a relative flow rate of the first flow of gas and the second flow of gas is adjustable.

7. The therapeutic powder applicator of claim 4, further comprising a second pressurized gas source, wherein the second pressurized gas source and the outlet are configured such that a second flow of gas from the second pressurized gas source flows through the outlet without flowing through the chamber.

8. The therapeutic powder applicator of claim 1, wherein the first pressurized gas source is a bellows.

9. The therapeutic powder applicator of claim 8, further comprising a first one-way valve configured to prevent backflow into the outlet when the bellows expand.

10. The therapeutic powder applicator of claim 9, further comprising a second one-way valve configured to fluidly connect the bellows with an exterior environment when the bellows expand.

11. The therapeutic powder applicator of claim 1, wherein a longitudinal axis of the chamber is parallel with an axis passing through the outlet.

12. The therapeutic powder applicator of claim 1, wherein a longitudinal axis of the chamber is angled relative to an axis passing through the outlet.

13. The therapeutic powder applicator of claim 1, further comprising a handle configured to rotate relative to the chamber.

14. The therapeutic powder applicator of claim 13, wherein the handle is configured to rotate about a rotation axis parallel to an axis passing through the outlet.

15. The therapeutic powder applicator of claim 13, wherein the first pressurized gas source is configured to rotate with the handle when the handle rotates relative to the chamber.

16. The therapeutic powder applicator of claim 13, wherein the handle is configured to rotate relative to the first pressurized gas source.

17. The therapeutic powder applicator of claim 1, further comprising a first gas inlet in fluid communication with the outlet through the plurality of pores of the distal portion of the chamber, wherein the first gas inlet is located adjacent to the proximal portion of the chamber.

18. The therapeutic powder applicator of claim 1, wherein the outlet is configured to be oriented at least partially vertically downwards during operation of the applicator such that the therapeutic powder is positioned adjacent to the distal portion of the chamber.

19. The therapeutic powder applicator of claim 1, wherein the porous membrane is constructed out of a woven material or a non-woven material.

20. The therapeutic powder applicator of claim 1, wherein the porous membrane is located adjacent to the outlet.

21. The therapeutic powder applicator of claim 1, wherein the proximal portion of the chamber is non-porous.

22. The therapeutic powder applicator of claim 1, further comprising one or more channels located between an exterior surface of the chamber and an interior surface of a housing of the applicator, wherein the first flow of gas from the first pressurized gas source flows through the one or more channels before entering the plurality of pores of the distal portion of the chamber.

23. A therapeutic powder applicator comprising:

a chamber configured to contain a therapeutic powder, wherein at least a distal portion of the chamber includes a porous membrane comprising a plurality of pores, and wherein the chamber is at least partially formed from the porous membrane such that the porous membrane defines a volume of the chamber and is configured to support the therapeutic powder during operation;

a first gas inlet; and an outlet in fluid communication with the chamber, wherein the first gas inlet is in fluid communication with the outlet through the plurality of pores of the distal portion of the chamber, wherein the distal portion of the chamber is located adjacent to the outlet, wherein the first gas inlet and the chamber are configured such that a first flow of gas from the first gas inlet flows around at least a proximal portion of the chamber before entering the plurality of pores of the distal portion of the chamber to entrain the therapeutic powder in the first flow of gas, and wherein the therapeutic powder applicator is configured to be a handheld applicator and the outlet is configured to deliver the therapeutic powder to a target area of a subject.

24. The therapeutic powder applicator of claim 23, further comprising the therapeutic powder disposed in the chamber.

25. The therapeutic powder applicator of claim 24, wherein the therapeutic powder is a hemostatic powder.

26. The therapeutic powder applicator of claim 23, further comprising a first conduit extending between the first gas inlet and the chamber.

27. The therapeutic powder applicator of claim 26, further comprising a second conduit extending between the first gas inlet and the outlet such that a second flow of gas flows through the outlet without flowing through the chamber.

28. The therapeutic powder applicator of claim 27, further comprising a variable flow resistance disposed along the first and/or second conduit.

29. The therapeutic powder applicator of claim 26, further comprising a second gas inlet, wherein the second gas inlet and the outlet are in fluid communication such that a second flow of gas from the second gas inlet flows through the outlet without flowing through the chamber.

30. The therapeutic powder applicator of claim 23, further comprising a bellows in fluid communication with the first gas inlet.

31. The therapeutic powder applicator of claim 23, wherein a longitudinal axis of the chamber is parallel with an axis passing through the outlet.

32. The therapeutic powder applicator of claim 23, wherein a longitudinal axis of the chamber is angled relative to an axis passing through the outlet.

33. The therapeutic powder applicator of claim 23, further comprising a handle configured to rotate relative to the chamber.

34. The therapeutic powder applicator of claim 33, wherein the handle is configured to rotate about a rotation axis parallel to an axis passing through the outlet.

35. The therapeutic powder applicator of claim 33, wherein the first gas inlet is configured to rotate with the handle when the handle rotates relative to the chamber.

36. The therapeutic powder applicator of claim 33, wherein the handle is configured to rotate relative to the first gas inlet.

37. The therapeutic powder applicator of claim 23, further comprising a bellows coupled to the first gas inlet, further comprising a first one-way valve configured to prevent backflow into the outlet when the bellows expand.

38. The therapeutic powder applicator of claim 37, further comprising a second one-way valve configured to fluidly connect the bellows with an exterior environment when the bellows expand.

39. The therapeutic powder applicator of claim 23, wherein the first gas inlet is located adjacent to the proximal portion of the chamber.

40. The therapeutic powder applicator of claim 23, wherein the outlet is configured to be oriented at least partially vertically downwards during operation of the applicator such that the therapeutic powder is positioned adjacent to the distal portion of the chamber.

41. The therapeutic powder applicator of claim 23, wherein the porous membrane is constructed out of a woven material or a non-woven material.

42. The therapeutic powder applicator of claim 23, wherein the porous membrane is located adjacent to the outlet.

43. The therapeutic powder applicator of claim 23, wherein the proximal portion of the chamber is non-porous.

44. A method of applying a therapeutic powder, the method comprising:

flowing a first gas flow around at least a proximal portion of a chamber before flowing the first gas flow through a plurality of pores of a porous membrane disposed at a distal portion of the chamber containing the therapeutic powder, wherein the chamber is at least partially formed from the porous membrane such that the porous membrane defines a volume of the chamber and is configured to support the therapeutic powder during operation;

entraining the therapeutic powder in the first gas flow;

flowing the entrained therapeutic powder through an outlet in fluid communication with the chamber, wherein the distal portion of the chamber is located adjacent to the outlet; and delivering the therapeutic powder from the outlet to a target area of a subject.

45. The method of claim 44, further comprising flowing a second gas flow through the outlet without flowing through the plurality of pores of the chamber.

46. The method of claim 45, further comprising adjusting a relative flow rate of the first gas flow and the second gas flow.

47. The method of claim 46, further comprising adjusting a spread of the therapeutic powder as the therapeutic powder is dispensed from the outlet.

48. The method of claim 45, further comprising supplying the first gas flow from a first pressurized gas source, and supplying the second gas flow from a second pressurized gas source.

49. The method of claim 44, further comprising compressing a bellows to supply the first gas flow.

50. The method of claim 49, wherein compressing the bellows to supply the first gas flow comprises flowing the first gas flow through a first one-way valve configured to prevent backflow into the outlet when the bellows expand.

51. The method of claim 50, further comprising releasing the bellows to reinflate the bellows by flowing a second gas flow from an exterior environment through a second one-way valve.

* * * * *